US00PP12314P2

(12) United States Plant Patent
Demaline

(10) Patent No.: US PP12,314 P2
(45) Date of Patent: Jan. 1, 2002

(54) MALE HOLLY PLANT NAMED 'WILLEMER'

(75) Inventor: Thomas L. Demaline, Avon, OH (US)

(73) Assignee: Willoway Nurseries, Inc., OH (US)

( * ) Notice: Subject to any disclaimer, the term of this patent is extended or adjusted under 35 U.S.C. 154(b) by 0 days.

(21) Appl. No.: 09/500,689

(22) Filed: Feb. 9, 2000

(51) Int. Cl.[7] ..... A01H 5/00
(52) U.S. Cl. ..... Plt./247
(58) Field of Search ..... Plt./247

*Primary Examiner*—Bruce R. Campell
(74) *Attorney, Agent, or Firm*—Renner, Otto, Boiselle & Sklar, LLP

(57) ABSTRACT

A male holly plant named WillEmer, a broadleafed evergreen shrub characterized by its dense, compact habit and small leaves.

4 Drawing Sheets

The present invention relates to a new and distinct variety of a male broadleafed evergreen or holly plant, Ilex hybrid.

'WillEmer' has a very dense, compact habit, reaching no more than 4 feet high and 6 feet wide at maturity. The leaves of 'WillEmer' are small size compared to similar varieties of holly plants and have 14 to 22 spines on their outer perimeter, with immature leaves having more spines than mature leaves. These spines range in length from 1 to 4 millimeters. The leaves emerge a yellow green color deepening to medium olive green. Mature growth is deep olive green. In winter the leaves gradually turn to a deep grey red, beginning at the midrib and working towards the edge. 'WillEmer' has deep red leaf buds that are formed in the fall. The flower buds are white with a slight pink cast and open to small, dioecious white flowers in the spring.

The following charateristics distinguish WillEmer from other male holly plants:

1. WillEmer has a dense, compact habit, reaching no more than 4 feet high and 6 feet wide at maturity.
2. WillEmer has leaves that are smaller than those of similar varieties of holly plants.

The original parent specimen of WillEmer was found by me as a seedling in a cultivated area at Avon in Lorain County, Ohio. This WillEmer has been propagated asexually at Avon, Ohio by way of rooted, semi-hardwood cuttings, perpetuating the original characteristics of the original plant.

Referring now to the accompanying drawings.

Figure 1:
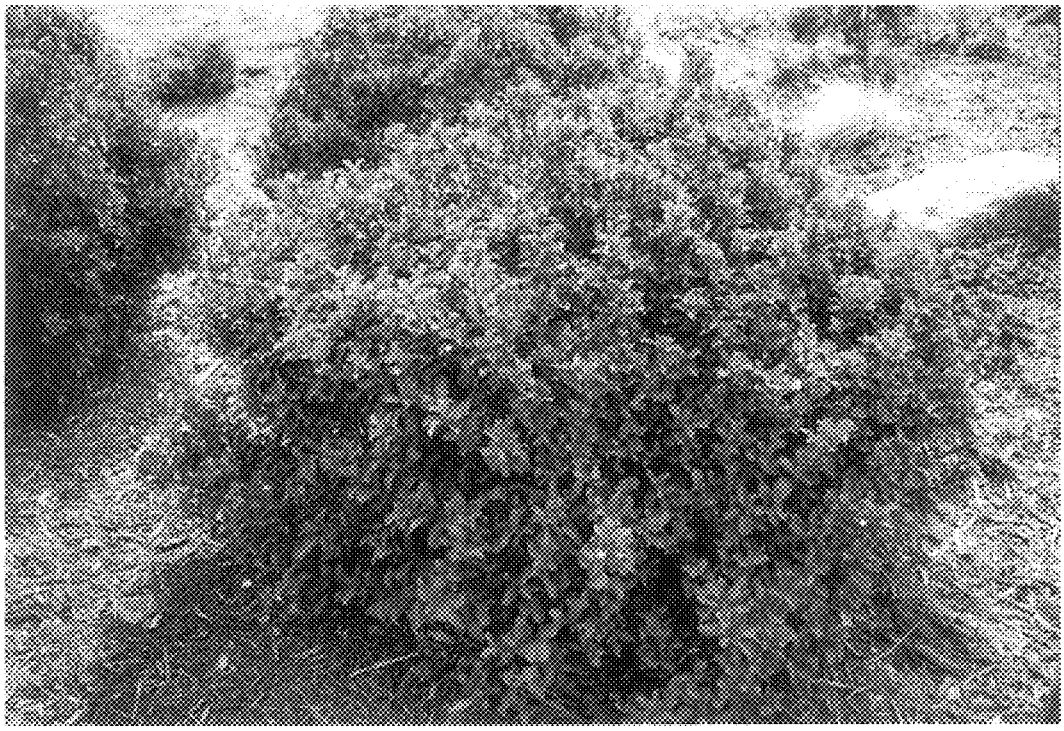
FIG. 1 is a colored photograph illustrating in perspective view the overall appearance of this WillEmer at maturity.
Figure 2:
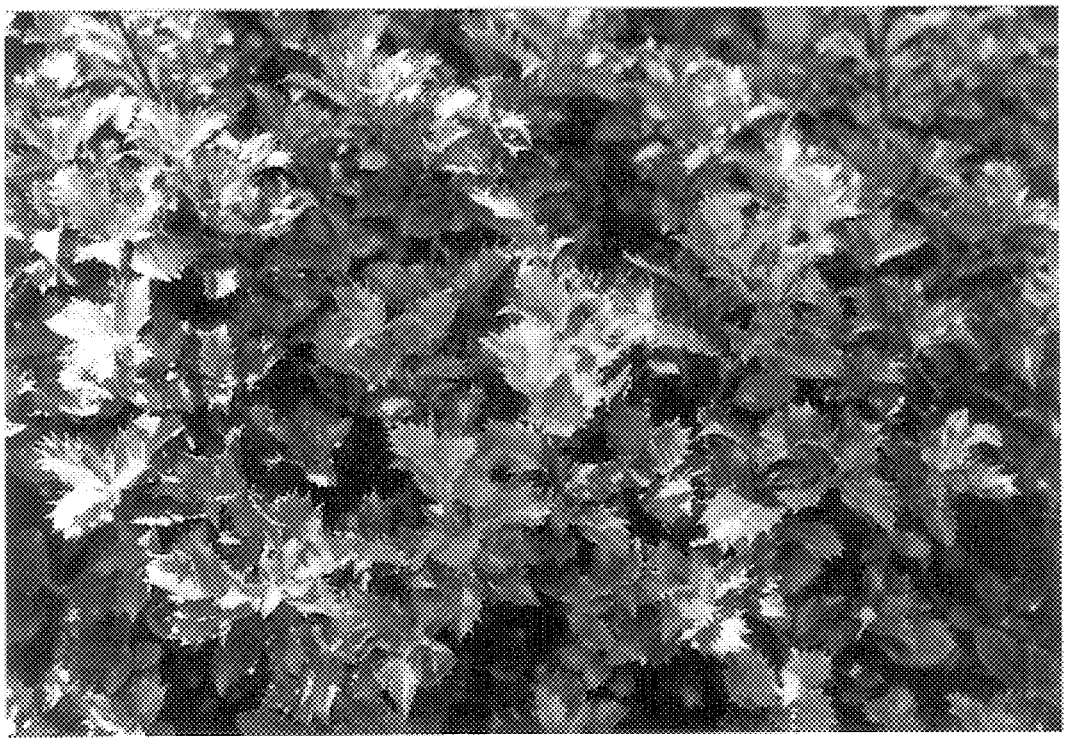
FIG. 2 is a colored photograph illustrating a close-up view of the foliage of WillEmer, depicting color, density and size of leaves.
Figure 3:
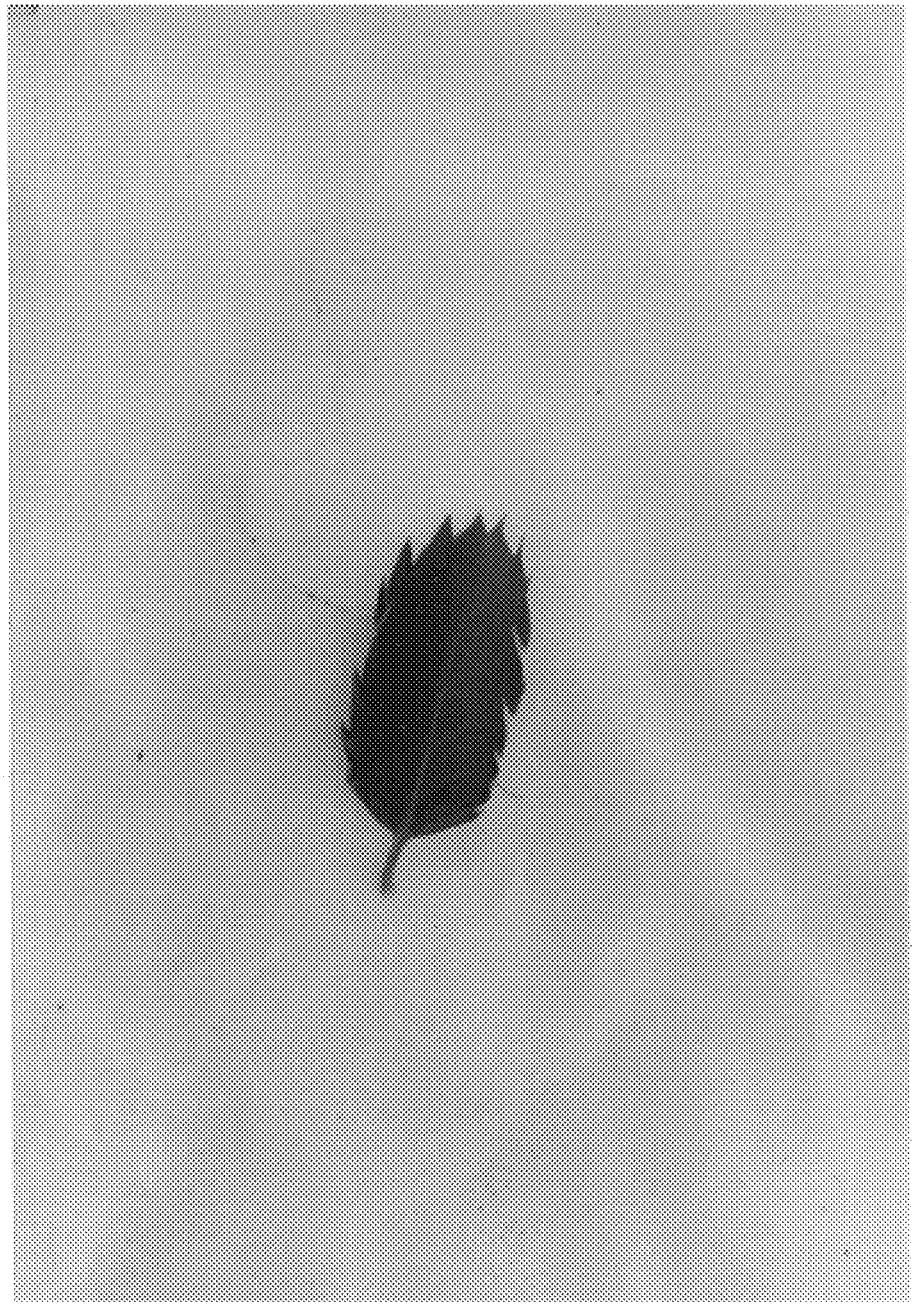
FIG. 3 is a colored photograph illustrating an individual leaf of WillEmer at maturity.
Figure 4:
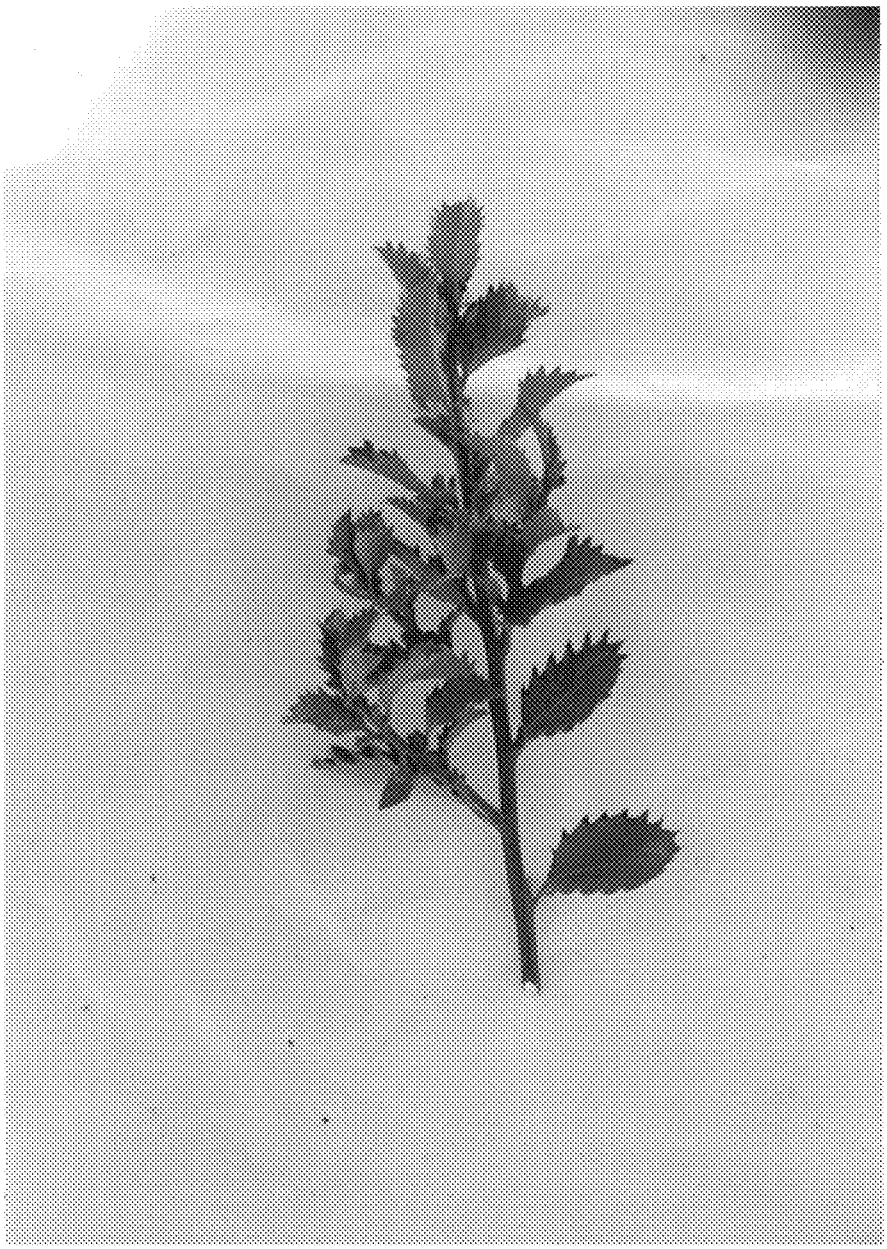
FIG. 4 is a colored photograph of a portion of the stem of WillEmer, depicting color of petioles and flower buds.

All four drawing figures show the colors as true as is reasonably possible to obtain in colored reproductions of this type.

The following is a detailed description of my new cultivar WillEmer. The age of the observed 'WillEmer' fourteen years old and is located at Avon, Ohio. Where color is different from the typical and is considered a distinguishing feature of this variety, where possible reference is made to specific colors on ISCC-NBS Color-Name Charts illustrated with Centroid Colors, a supplement to NBS Circular 553.

Botanical description:

*Parentage.*—Unknown — obtained as a seedling found in a cultivated are at Avon in Lorain County, Ohio.

*Form/size.*—A broadleafed evergreen having a dense compact habit reaching no more than four feet high and six feet wide at maturity.

*Growth rate.*—3–4 inches per year. Reaches maturity in approximately 8–10 years. The observed 'WillEmer' is located at Avon, Ohio, is fourteen years old, and has a height of approximately four feet and a spread of approximately six feet.

*Trunk.*—Mature trunk is deep grey olive green (color 128) with brown striping and is approximately 5.2 cm. in diameter. New growth is on deep yellow green (color 118) stems and has a smooth surface texture. Mature bark has a semi-smooth surface texture.

*Leaves.*—3–4 cm. in length, 1–2 cm. wide and 0.5 mm. thick. Reddish petioles are 5–6 mm. long and 1–2 mm. thick. Leaves have 14–22 spines ranging in length from 1–4 mm., with immature leaves having more spines than mature leaves. Leaf buds forming in the fall are a deep red (color 14) approximately 0.15 mm. wide and 4 mm. long. New leaf growth is yellow green (color 117) to deep yellow green (color 118) deepening to medium olive green (color 125). Mature growth is deep olive green (color 126). Leaves are serrate in shape with insignificant veining. In winter the leaves gradually turn to deep grey red (color 20), beginning at the midrib and working towards edge.

*Flowers.*—Flower buds are white with a slight pink cast. In spring flower buds swell, opening to small, dioecious white flowers approximately 0.5 cm. in diameter. The flowers are four petal white with four light yellow (color 86) anthers. Flowers bloom from leaf axles similar to the structure of a cyme inflorescence.

*Hardiness.*—Hardy in USDA Hardiness Zone 5. Appears to be very disease/insect resistant.

I claim:

1. A male holly plant named WillEmer, as described and illustrated, a broadleafed evergreen characterized by its dense, compact habit and small leaves.

* * * * *